United States Patent [19]

Ross

[11] Patent Number: 5,269,023
[45] Date of Patent: Dec. 14, 1993

[54] BODY WARMING DEVICE

[76] Inventor: Eugene B. Ross, Rte. 4, Box 120, Laurens, S.C. 29360

[21] Appl. No.: 734,897

[22] Filed: Jul. 24, 1991

[51] Int. Cl.$^5$ .............................................. A41D 5/00
[52] U.S. Cl. ........................................... 2/66; 2/162; 2/208; 2/158; 126/204
[58] Field of Search ........................ 2/162, 17, 66, 208, 2/158, DIG. 1, DIG. 2; 224/224, 226; 126/204

[56] References Cited

U.S. PATENT DOCUMENTS

| | | | |
|---|---|---|---|
| 2,014,256 | 9/1935 | Kramer | 2/66 |
| 2,384,285 | 9/1945 | Deutsch | 2/17 |
| 2,725,564 | 12/1955 | Dering | 2/66 |
| 2,727,241 | 12/1955 | Smith | 2/66 |
| 2,835,896 | 5/1958 | Giese | 2/66 |
| 3,793,643 | 2/1974 | Kinoshita | 2/66 |
| 4,408,355 | 10/1983 | Brock | 2/66 |
| 4,495,659 | 1/1985 | Madnick et al. | 2/66 |
| 4,862,519 | 9/1989 | Bull | 2/66 |
| 4,949,887 | 8/1990 | Holmes | 2/66 X |
| 5,139,187 | 8/1992 | Fowler | 2/162 X |

FOREIGN PATENT DOCUMENTS 259599  7/1928  Italy ............................................ 2/66

*Primary Examiner*—Clifford D. Crowder
*Assistant Examiner*—Gloria Hale
*Attorney, Agent, or Firm*—Cort Flint

[57] ABSTRACT

A body warming device (A) is disclosed which warms a person's hands or other body portion that includes a flattened tubular covering (B) having open ends (12, 14) which lead to hand warming pockets (32, 36) on opposing sides of a heater pouch (C) containing an air activated heat pack (30). An air tight compartment (D) provides for deactivation and storage of the heat pack for reuse. Covering (B) may be fastened in a first configuration wherein heater pouch (C) is inside the tubular covering for warming the hands, and a second configuration wherein the heater pouch (C) is on the outside of the covering for direct placement and warming of other portions of the body as a therapeutic device.

25 Claims, 2 Drawing Sheets

BODY WARMING DEVICE

BACKGROUND OF THE INVENTION

The invention relates to a heater device for warming a portion of a person's body, and particularly to such a device for warming the hands of a person outdoors, such as a golfer, hunter, fisherman, or other outdoors person.

Heretofore, numerous devices have been proposed for warming the hands and other portions of the body of a person. For example, U.S. Pat. No. 4,862,519 discloses a hand warmer pack which is worn about a person's waist. A muff is provided on the outside of the pack which includes a flannel pocket which may contain a heater. The construction is quite bulky and is not suitable for certain types of outdoor activities. U.S. Pat. No. 4,408,355 discloses another hand warming device which is worn about the waist that includes end openings through which the hands may be placed within the device for warming. A heat source may be provided inside the muff as an additional means of warming the hands. The device protrudes significantly from the body and can interfere with a person's activities. U.S. Pat. Nos. 4,495,659 and 2,727,241 disclose muff-type hand warmers which may be carried or worn about a portion of a person's body that include pockets for chemical heaters and the like inside the muff. While the foregoing devices provide suitable hand warmers, they are rather bulky and awkward to wear. In particular, the prior art devices may not be suitably worn by persons engaged in certain activities, such as golfing and other sporting activities.

Golfers often use a chemical heat pack activated by air to warm their hands in the winter months. The heat packs typically last about eighteen hours but are only used for a small fraction of that time and discarded. For example, see U.S. Pat. No. 4,282,005. U.S. Pat. No. 4,949,887 discloses an insulated multi-use seat cushion with closeable hand and foot openings for warming wherein a closeable flap is provided as a heat window to adjust the amount of heat released by an auxiliary heater and the like.

Accordingly, an important object of the present invention is to provide a body warming device which may be conveniently worn by a person engaged in activities outdoors for warming the hands.

Another object of the present invention is to provide a body warming device which may be worn by a person to warm the hands and may be reversed to place the warmer directly against the body to warm other portions of the body.

Another object of the present invention is to provide a body warming device which uses a chemical heat pack activated by air for warming a portion of a person's body which includes an air-tight compartment which deactivates and stores the chemical heat pack for later use, thus eliminating the waste of an unused heat pack.

Another object of the invention is to provide a body warming device for warming the hands and other body portions which has a generally flat profile so that it does not protrude from the body and does not unduly interfere with a person's activities.

Another object of the invention is to provide a body warming device for warming the hands of a golfer or other outdoor sportsman which may be worn about the person's body without interfering with the person's activities.

SUMMARY OF THE INVENTION

The above objectives are accomplished according to the present invention by providing a body heater device for warming a portion of a person's body comprising a tubular covering defined by at least first and second flexible panels folded in a generally flattened tubular configuration. An air permeable heater pouch is carried within the tubular covering for containing a chemical heat pack activated by air. A first fastener is carried by the first panel, and a second fastener is carried by the second panel. The first and second fasteners fasten the first and second panels together to form the tubular covering. The flattened tubular configuration has opposed end openings and does not obstruct a person's activities. The heater pouch is carried within the tubular covering defining a first hand warming pocket between a first side of the pouch and the first panel, and a second hand warming pocket between a second side of the heater pouch. The first and second panels have a first fastened configuration in which the heater pouch is carried within the tubular covering for warming the hands. The first and second panels have a second fastened configuration in which the heater pouch is carried outside of the tubular covering for contacting and warming another portion of the person's body. The first fastener is carried on an interior side of the first panel, and the second fastener is carried on an exterior side of the second panel. A closed compartment generally impervious to air is included in the tubular covering for containing the heat pack in a generally air tight manner to deactivate the heat pack when placed in the compartment. An auxiliary compartment is carried by the tubular covering for carrying miscellaneous items. A strap assembly is provided for attaching the tubular covering to a person's body. The strap assembly includes connector tabs affixed to the covering near the pouch which include upper, generally straight edges for fastening the strap as a belt around a person's body or around the neck. The connector tabs include lower, upwardly angled edges for fastening the strap around an upper portion of a person's body such as the shoulders. The strap includes at least one adjustable strap connected to the covering which has a first connector, and a second connector which connects to the first connector is attached near the covering so that the strap may be adjusted to a relatively small diameter for fitting about a limb of a person's body.

DESCRIPTION OF THE DRAWINGS

The construction designed to carry out the invention will hereinafter be described, together with other features thereof.

The invention will be more readily understood from a reading of the following specification and by reference to the accompanying drawings forming a part thereof, wherein an example of the invention is shown and wherein.

DESCRIPTION OF A PREFERRED EMBODIMENT

Figure 1:
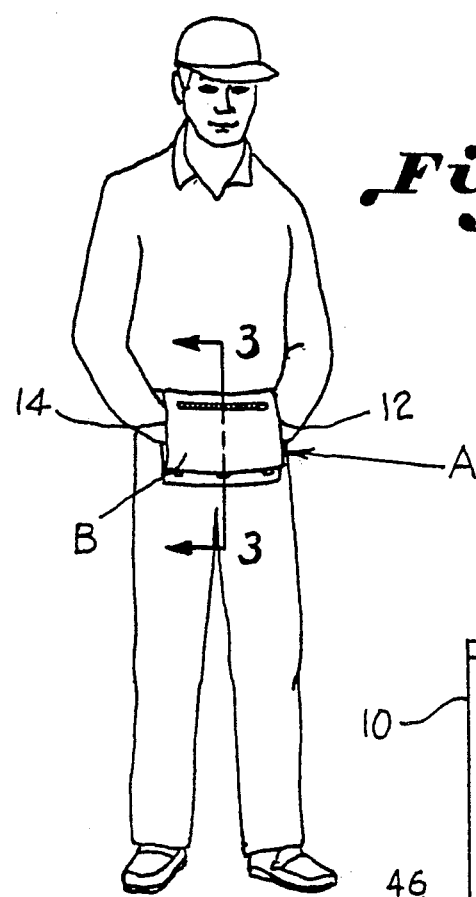
FIG. 1 is a perspective view illustrating an outdoorsman wearing a body warming device constructed in accordance with the present invention.

Referring now in more detail to the drawings, a body warming device is illustrated, designated generally as A, which includes a tubular covering B formed by an elongated covering 10 which may be folded into a flattened tubular configuration having opened ends 12 and 14 for receiving the hands of a person, as can best be seen in FIG. 1. In the illustrated embodiment, covering 10 includes at least a first panel 16 and a second panel 18. Preferably, the covering includes an intermediate panel 19 which may be folded about fold lines 20 and 22 to provide the tubular configuration, as can best be seen in FIG. 3. Fold lines 20 and 22 are preformed by stitching, but covering 10 may also be one-piece and fold naturally when the ends are fastened. Intermediate panel 19 and second panel 18 may also include a single panel without a stitch line. Covering 10 is preferably a two layer covering which is stitched at 24 about its perimeter. There is a first fastener means 26 carried by first panel 16 and a second fastener means 28 carried by second panel 18. Preferably, the first and second fastening means include elongated strips of Velcro TM fastening material. For example, first fastener means 26 may include Velcro TM hook material and second fastener means 28 may include Velcro TM loop material.

Figure 2:
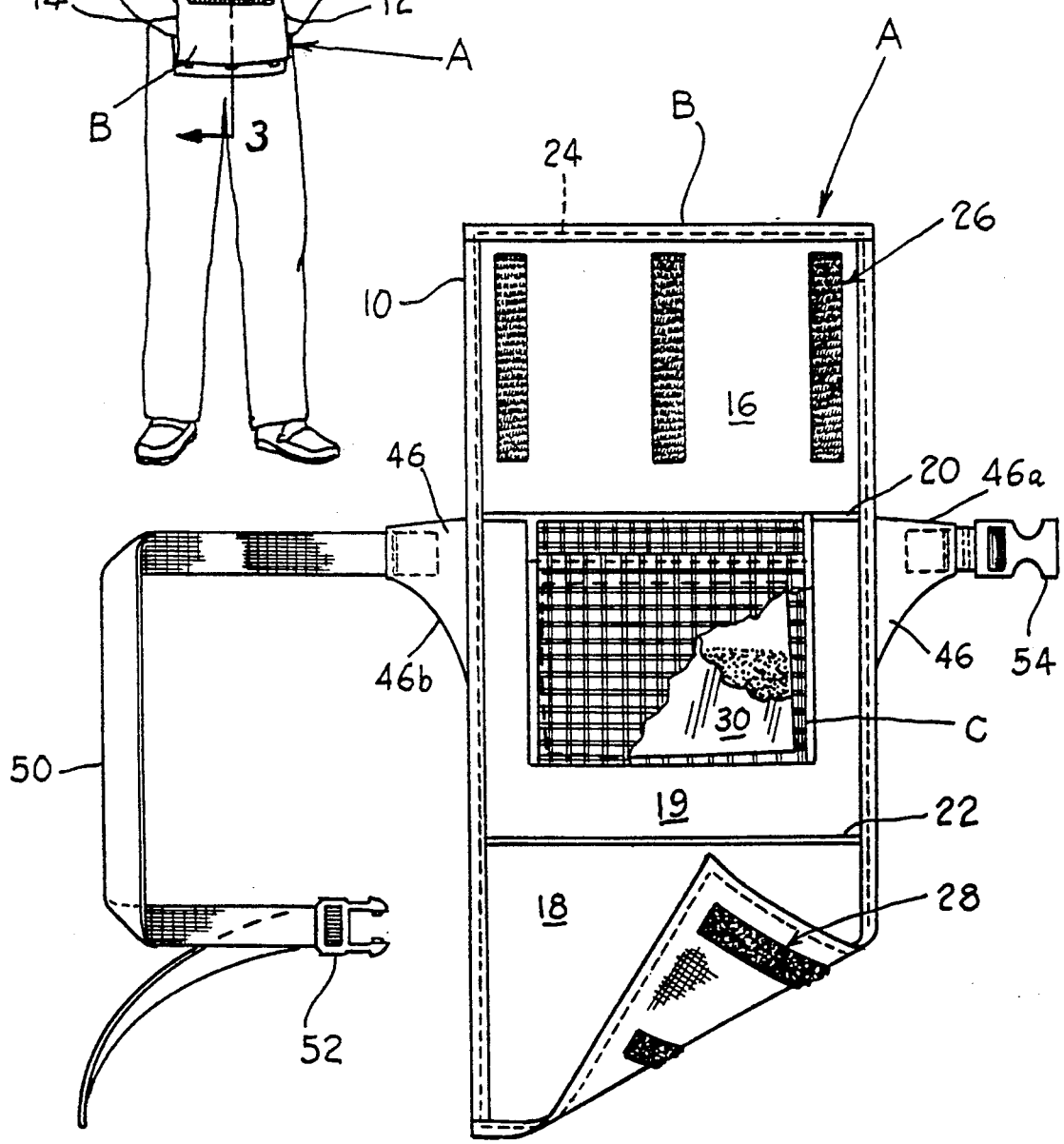
FIG. 2 is a plan view illustrating a body warming device according to the invention in an unfolded configuration.
Figure 3:
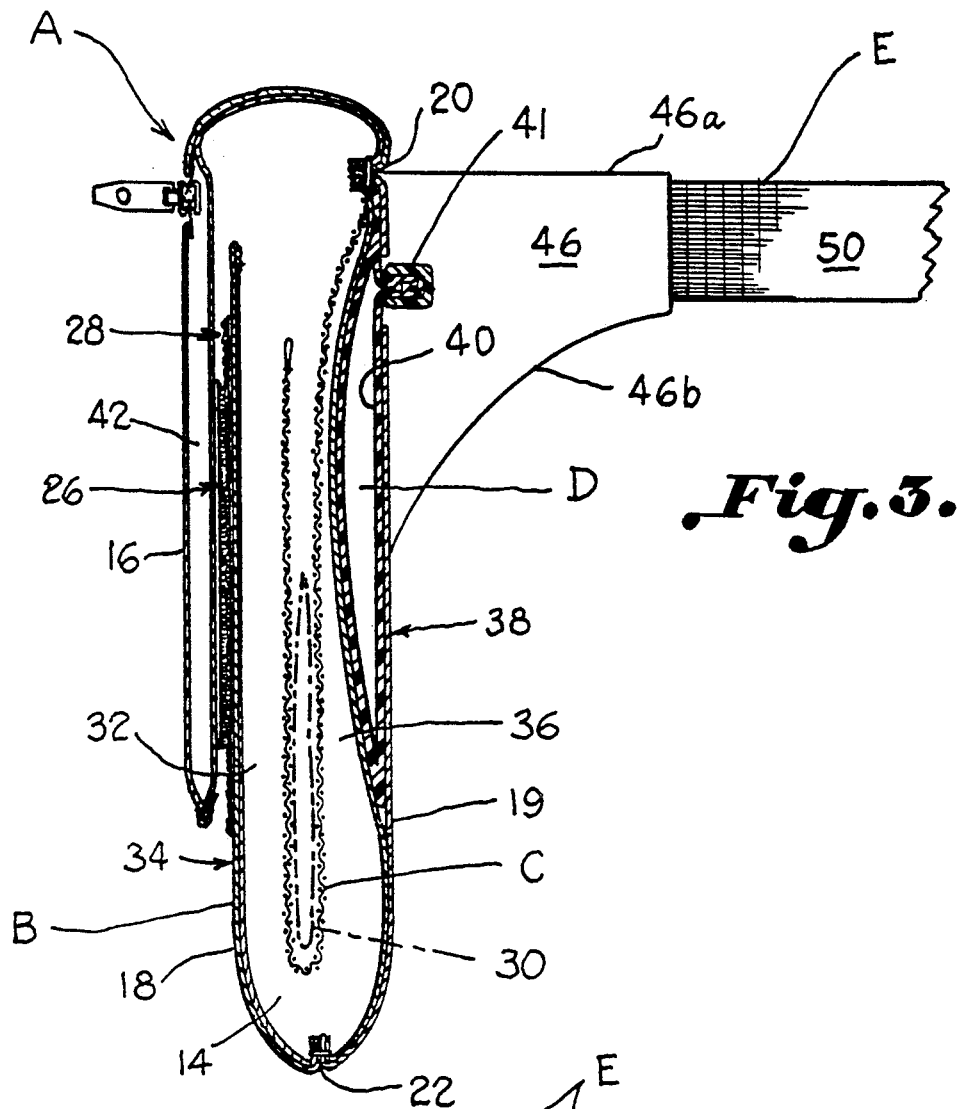
FIG. 3 is a sectional view taken along line 3—3 of FIG. 1.

Carried by tubular covering B is a heater pouch C which is air permeable for containing a chemical heat pack 30 which is activated by air such as shown in U.S. Pat. No. 4,282,005. Preferably, heater pouch C is constructed from an open mesh material such as netting or woven flannel. As can best be seen in FIG. 2, in the illustrated embodiment, heater pouch C is carried by intermediate panel 19 and may be secured thereto along a line below fold line 20 such as by stitching. In this configuration, heater pouch C hangs in a suspended configuration when body warming device A is worn about the person's body, as can best be seen in FIG. 3. In this manner, there is a first hand warming pocket 32 formed between a first side 34 of tubular covering B and heater pouch C; and a second hand warming pouch 36 defined between a second side 38 of the tubular covering and heater pouch C. First side 34 is formed by first panel 16 overlapping and secured to second panel 18. Second side 38 is defined by intermediate panel 19. While tubular covering B is shown having three panels, the same can be a one-piece panel folded upon itself with ends fastened generally as illustrated in FIG. 3.

There is a closed compartment D carried by tubular covering B which is generally impervious to air for containing chemical heat pack 30 in a generally air tight manner to deactivate the heat pack when it is placed in the compartment and not in use. For this purpose, compartment D may include plastic sheeting 40 cemented between the layers of intermediate panel 19, and provided with a fluid tight closure 41, such as disclosed in U.S. Pat. No. 4,672,723. The closed compartment D may be formed in, or on, another panel of the tubular covering as well. Closed compartment D provides the expedient that once heater pack 30 is activated by exposure to air, it need not be discarded when its present use is over, but may be deactivated and saved for a later use. Typically, the heat pack produces heat much longer than is necessary for the particular activity. For example, a golfer may use the heater pack for four to five hours with twelve or more hours of heat remaining in the heat pack. The golfer may not need the chemical heat pack during the entire round of golf. In either event, the golfer or other outdoors activist may place the opened heat pack in the air tight compartment D and deactivate the heat pack until further use is desired. An auxiliary compartment 42 may be included in first panel 16 for carrying miscellaneous items such as extra heat packs.

Strap means E is provided for fastening the tubular covering about the waist of a person, as illustrated at FIG. 1, or for wearing the tubular covering about the shoulders or neck of a person. For this purpose, strap means E includes a pair of strap tab connectors 46 having straight edges 46a which enables a good fit for wearing the tubular covering as a belt around the person's waist. Alternately, tab connectors 46 include angled edges 46b which enable the strap to be comfortable worn about the shoulders without significantly distorting the configuration of the tubular covering. As can best be seen in FIG. 2, strap means E includes a strap 50 connected to one of the tab connectors, having an adjustable connector 52 carried at a remote end. The opposite tab connector 46 includes a second connector 54 which mates with connector 52. Connector 54 is attached directly to tab connector 20 so that adjustable strap 50 may be shortened substantially and fastened to connector 54 to make a small loop for fitting the device about a limb of the person.

Figure 4:
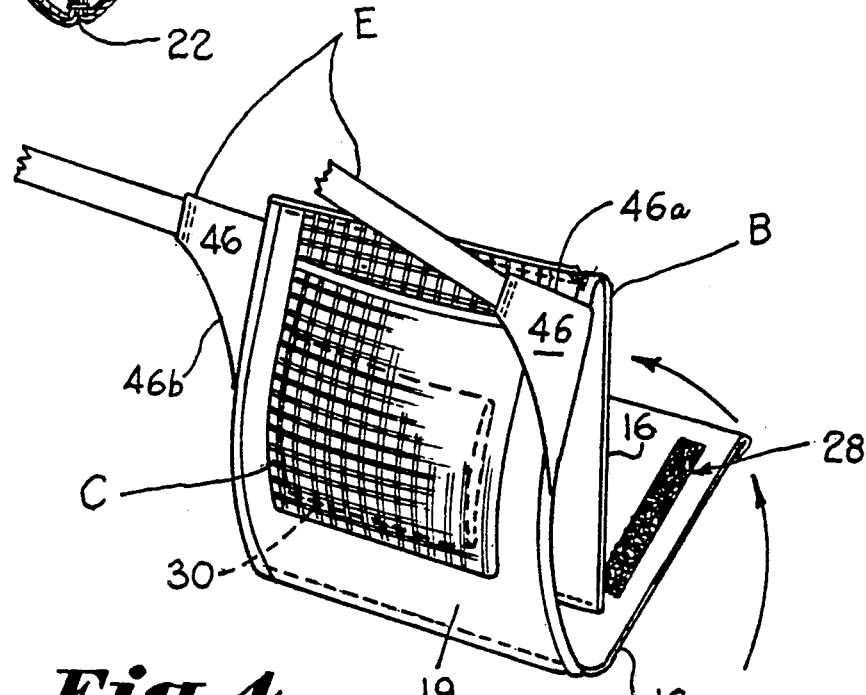
FIG. 4 is a perspective view illustrating a body warming device constructed according to the present invention in a reverse folded configuration for directly warming a portion of a person's body.

As can best be seen in FIG. 4, first and second fasteners 26 and 28 provide fastening of the tubular covering in two configurations. A first fastened configuration fastens the tubular covering in the configuration illustrated in FIG. 3 wherein heater pouch C is within an interior of the tubular covering for warming the hands or other extremities of a person's body. In FIG. 4, tubular covering B is fastened in a second fastened configuration in which heater pouch C is on the outside of tubular covering B so that it may be worn directly against a portion of a person's body for warming. For example, the warming device may be quite comfortably worn about the back of a person having a back ache or back pain for comfort. The heater pouch may be placed directly against any portion of a person's body to which direct heat is to be applied. Preferably, the insides of the panel covering, as illustrated in FIG. 3, include a soft, warm flannel lining so that when used as a hand warmer, the hands are between the soft lining and the heater pouch. This soft, warm lining would also be against the person's body when the warming device is used in the second fastened configuration of FIG. 4, and may be used for sitting. For the above purposes, fasteners 26 and 28 are preferably elongated strips covering a substantial dimension of panels 16, 18 so that the panels are secured together tightly and flatly in either configuration.

Thus, it can be seen that an advantageous construction for a body warming device can be had according to the invention where in a tubular covering can be used in a generally flattened configuration that does not interfere with activity of a person, such as golfing, or other outdoor activities. The flattened tubular configuration is opened at both ends for easy entry of the hands for warming, the configuration also allows for reversal of the tubular coverings so that the heater pouch may be worn on the outside for directly warming a person's body. Quite advantageously, the chemical heat pack used in the warming device may be deactivated by placing the heat pack in an air tight compartment for later use. Thus, a highly efficient body warming device is provided.

While a preferred embodiment of the invention has been described using specific terms, such description is for illustrative purposes only, and it is to be understood that changes and variations may be made without departing from the spirit or scope of the following claims.

What is claimed is:

1. A body warming device for warming a portion of a person's body comprising:
   a planar covering being foldable into a tubular covering defined by at least first and second flexible panels of said planar covering folded generally next to each other;
   an air permeable heater pouch carried within an interior of said tubular covering for containing a chemical heat pack activated by air;
   first fastening means carried by said first panel;
   second fastening means carried by said second panel;
   said first and second fastening means fastening said first and second panels together to form said tubular covering with said first and second panels fastened and arranged in a generally flattened tubular configuration having opposed end openings so that said covering does not obstruct said person's activity;
   said heater pouch being carried within said flattened tubular covering and depending downwardly a substantial distance over at least half of the height of one of said first and second panels to define a first hand warming pocket between a first side of said pouch and said first panel and a second hand warming pocket between a second side of said pouch and said second panel for receiving and warming the hands of said person; and
   strap means for carrying said tubular covering on a persons body.

2. The device of claim 1 including an intermediate panel defined between said first and second panels; and
   a first fold formed between said first panel and intermediate panels, and a second fold formed between said second and intermediate panels.

3. The device of claim 1 wherein said first and second panels having a first fastened configuration in which said pouch is carried within said tubular covering for warming said hands, and said first and second panels having a second fastened configuration in which said pouch is carried outside of said tubular covering for contacting and warming another portion of said person's body.

4. The device of claim 3 wherein said first and second fastening means fasten said first and second panels in both of said first and second fastened configurations.

5. The device of claim 4 wherein said first fastening means is carried on an interior side of said first panel, and said second fastening means is carried on an exterior side of said second panel.

6. The device of claim 1 including a closed compartment generally impervious to air carried by said tubular covering for containing said heat pack in a generally air tight manner to deactivate said heat pack when placed in said compartment.

7. The device of claim 1 including an auxiliary compartment carried by said tubular covering for carrying miscellaneous items.

8. The device of claim 1 wherein said strap means includes a strap, and a pair of connector tabs affixed to said covering which include generally straight upper edges for fastening said strap as a belt around said person's body, and said connector tabs include lower upwardly angled edges for fastening said strap around an upper portion of said person's body.

9. The device of claim 8 wherein said strap means includes at least one adjustable strap connected to said covering having a first connector, and a second connector which connects to said first connector is attached near said covering so that said adjustable strap may be adjusted to a relatively small loop for fitting about a limb of said person's body.

10. A body warming device for warming a portion of a person's body comprising:
    an elongated planar flexible covering which may be folded into a tubular covering;
    fastening means for fastening said covering in first and second configurations in which a generally flattened tubular covering is defined having first and second end openings;
    an air permeable heater pouch carried within said covering for containing a heater for warming said portion of said person's body when said tubular covering is in said first configuration;
    a first side of said tubular covering defined on a first side of said pouch and a second side of said tubular covering defined on a second side of said pouch in said first configuration of said tubular covering, and; said first and second sides being configured interiorally of said tubular cover in said first configuration;
    said first and second covering sides being configured exteriorally of said tubular covering in said second configuration of said tubular covering;
    said tubular covering having said first configuration wherein said heater pouch is carried within said tubular covering for warming said hands, and said tubular covering having said second configuration wherein said heater pouch is carried outside of said tubular covering for contacting and warming another portion of said person's body; and
    strap means for carrying said tubular covering on said person's body.

11. The device of claim 10 including a closed compartment generally impervious to air carried by one of said first and second sides for containing said heat pack in a generally air tight manner to deactivate said heat pack when placed in said compartment.

12. The device of claim 10 wherein said heater pouch is carried within said tubular covering in said first fastened configuration defining first and second hand warming pockets on opposing sides of said pouch for receiving and warming the hands of said person extended through said first and second openings.

13. The device of claim 12 wherein said covering includes first and second panels defined on opposing sides of said heater pouch, and said fastening means includes first and second fastening means carried by said first and second panels respectively which fastens said covering in said first and second configurations.

14. The device of claim 13 wherein said first fastening means is carried on an interior side of said first panel, and said second fastening means is carried on an exterior side of said second panel.

15. The device of claim 10 including an auxiliary compartment carried by said tubular covering for carrying miscellaneous items.

16. The device of claim 10 wherein said strap means includes a strap, and a pair of connector tabs affixed to said covering which include generally straight upper edges for fastening said strap as a belt around said person's body, and said connector tabs include lower upwardly angled edges for fastening said strap around an upper portion of said person's body.

17. The device of claim 16 wherein said strap means includes at least one adjustable strap connected to said covering having a first connector, and a second connector which connects to said first connector is attached near said covering so that said adjustable strap may be adjusted to a relatively small loop for fitting about a limb of said person's body.

18. A body warming device for warming a portion of a person's body comprising:
 a tubular covering including a first side and a second side defined by flexible side panels;
 an air permeable heater pouch carried by said tubular covering for containing a chemical heat pack activated by air;
 said heater pouch being carried within said tubular covering for warming said hands; and
 a closed compartment generally impervious to air carried by one of said first and second sides for containing said heat pack in a generally air tight manner to deactivate said heat pack when placed in said compartment.

19. The device of claim 18 wherein said tubular covering includes a pair of free ends, and including fastening means carried by said covering for fastening said cover together near said free ends to define said tubular covering.

20. The device of claim 18 including strap means for carrying said tubular covering on a persons body.

21. The device of claim 18 wherein said covering includes first and second panels having a first fastened configuration in which said pouch is carried within said tubular covering for warming said hands, said first and second panels having a second fastened configuration in which said pouch is carried outside of said tubular covering for contacting and warming another portion of said person's body, and fastening means for fastening said covering in said first and second configurations.

22. The device of claim 21 wherein said first and second fastening means fastens said first and second panels in both of said first and second fastened configurations.

23. The device of claim 22 wherein said first fastening means is carried on an interior side of said first panel, and said second fastening means is carried on an exterior side of said second panel.

24. The device of claim 18 wherein said strap means includes a strap, and a pair of connector tabs affixed to said covering which include generally straight upper edges for fastening said strap as a belt around said person's body, and said connector tabs include lower upwardly angled edges for fastening said strap around an upper portion of said person's body.

25. The device of claim 24 wherein said strap means includes at least one adjustable strap connected to said covering having a first connector, and a second connector which connects to said first connector is attached near said covering so that said adjustable strap may be adjusted to a relatively small loop for fitting about a limb of said person's body.

* * * * *